United States Patent [19]

Anderson et al.

[11] Patent Number: 4,873,367

[45] Date of Patent: Oct. 10, 1989

[54] METHOD FOR PREPARING 4-HYDROXY-3-PHENYLBENZOIC ACID

[75] Inventors: Patricia P. Anderson, Worthington, Mass.; Timothy M. Sivavec, Clifton Park; Tohru Takekoshi, Scotia, both of N.Y.

[73] Assignee: General Electric Company, Schenectady, N.Y.

[21] Appl. No.: 275,881

[22] Filed: Nov. 25, 1988

[51] Int. Cl.$^4$ .............................................. C07C 51/15
[52] U.S. Cl. ..................................... 562/425; 560/141
[58] Field of Search ................................ 562/425, 423

[56] References Cited

U.S. PATENT DOCUMENTS

| | | | |
|---|---|---|---|
| 1,915,429 | 6/1933 | Laska et al. | 562/425 |
| 1,969,355 | 8/1933 | Christiansen | 562/425 |
| 2,042,343 | 5/1935 | Kyrides | 562/425 |
| 3,660,372 | 5/1972 | Schoenewaldt | 562/425 |
| 3,681,445 | 8/1972 | Ruyle | 562/425 |

*Primary Examiner*—Paul J. Killos
*Attorney, Agent, or Firm*—William H. Pittman; James C. Davis, Jr.

[57] ABSTRACT

4-Hydroxy-3-phenylbenzoic acid is prepared by carbonation of a 2-phenylphenol alkali metal salt in the presence of a liquid N,N-dialkylcarboxamide such as dimethylformamide. Carbonation may be effected at atmospheric pressure or at superatmospheric pressures.

17 Claims, No Drawings

METHOD FOR PREPARING 4-HYDROXY-3-PHENYLBENZOIC ACID

This invention relates to the preparation of 4-hydroxy-3-phenylbenzoic acid, and more particularly to a method for its preparation which minimizes the proportion of isomers and by-products.

4-Hydroxy-3-phenylbenzoic acid is a useful intermediate for the preparation of thermotropic polyesters, many of which have liquid crystalline properties. Numerous possible methods for its preparation have been studied; the simplest of these is probably the Kolbe-Schmitt reaction of carbon dioxide with a salt of 2-phenylphenol. An attempt to prepare the compound in this way is described in Slotta et al., *Chem. Ber.*, 68, 2226 (1935), but it is stated that the principal products were dicarboxylic acids. It has subsequently been discovered that 4-hydroxy-3-phenylbenzoic acid is obtained under these conditions, but in admixture with dicarboxylated products and isomers such as the 2-hydroxy material. There is still a need, therefore, for a preparative method which affords the desired compound without by-product contamination in large amounts.

The present invention is based on the discovery that salts of 2-phenylphenol can be carboxylated in solution in certain dipolar aprotic solvents, namely substituted carboxamides. This method of carboxylation of various other substituted phenols is known; reference is made, for example, to Meek et al., *J. Chem. Eng. Data*, 14, 388 (1969); *C.A.*, 66, 37582 (1967); and *C.A.*, 69, 51797 (1968). However, the use of the method with 2-phenylphenol to produce 4-hydroxy-3-phenylbenzoic acid in a highly regioselective reaction is not suggested therein.

Accordingly, the invention is a method for preparing 4-hydroxy-3-phenylbenzoic acid which comprises contacting a mixture of an anhydrous alkali metal salt of 2-phenylphenol and a liquid N,N-dialkylcarboxamide, said mixture containing up to about 50% by weight of said salt, with carbon dioxide at a pressure of at least about one atmosphere and a temperature in the range of about 70°–150° C., and neutralizing the salt thus formed.

The essential reagent for use in the method of this invention is an anhydrous alkali metal salt of 2-phenylphenol. The sodium and potassium salts are preferred by reason of their availability and ease of preparation, with the potassium salt being particularly preferred since it reacts rapidly and with a particularly high degree of regioselectivity.

For maximization of reaction rate and yield, it is essential that the salt be anhydrous. Anhydrous alkali metal salts of 2-phenylphenol are not difficult to obtain, even when prepared in the presence of water; it is frequently convenient to employ a mixture of water and a relatively high boiling organic liquid and to remove the water by distillation. Such an operation is particularly effective when the organic liquid is one which forms an azeotrope with water, such as toluene. It is also possible to employ molecular sieves or other suitable drying agents during the reaction, to remove water.

The dipolar aprotic solvent used according to the invention is a liquid N,N-dialkylcarboxamide, with dimethylformamide and dimethylacetamide, especially the former, being preferred because of their availability and effectiveness.

The mixture of the alkali metal salt and amide should contain up to about 50% by weight of said salt. The use of salt concentrations higher than about 50% decreases the yield of 4-hydroxy-3-phenylbenzoic acid with an increase in isomer yields. Preferred concentrations are in the range of about 10–40%. Under these conditions, the salt ordinarily dissolves in the amide.

According to the invention, the salt-amide mixture is contacted with carbon dioxide. Contact may be effected by any known method, including passing the gas into the mixture at atmospheric pressure and pressurizing the gas with the mixture at pressures in the range of about 1–50 and preferably about 1–35 atmospheres.

Reaction temperatures in the range of about 70°–150° C. may be employed. At lower temperatures the reaction proceeds too slowly to be practical, while higher temperatures cause an increase in isomer formation at the expense of 4-hydroxy-3-phenylbenzoic acid. The preferred temperature range is about 80°–110° C.

The reaction between carbon dioxide and the 2-phenylphenol salt proceeds with the formation of a salt of the desired 4-hydroxy-3-phenylbenzoic acid. At lower pressures (e.g., about 1–5 atmospheres), the maximum conversion to the salt of the desired acid is about 50%, with the remaining 2-phenylphenol salt serving as a proton acceptor. Conversion increases with an increase in pressure, which apparently facilitates carbonation in the absence of a proton acceptor.

Conversion may also be increased by adding an anhydrous base to the reaction mixture when the carbonation reaction has ceased. Bases such as sodium amide and sodium hydride are useful for this purpose. In the absence of added base, it is possible to recycle unconverted 2-phenylphenol.

Following formation of the salt of 4-hydroxy-3-phenylbenzoic acid, it is usually preferred to remove unreacted 2-phenylphenol and non-polar and weakly polar by-products from the crude product. This may be conveniently achieved by extraction with a non-polar solvent such as toluene which is effective to dissolve said materials and the amide. There remains an insoluble crude solid or liquid product comprising chiefly the salt of 4-hydroxy-3-phenylbenzoic acid, which may be converted to the free acid by conventional neutralization.

The products obtained by the method of this invention typically contain 4-hydroxy-3-phenylbenzoic acid in amounts greater than 90% by weight, with the principal impurities being the 2-hydroxy isomer and various dicarboxylated products such as 4-hydroxy-5-phenylisophthalic acid. For certain purposes, said product may be usable in its crude form; however, it is frequently desired to obtain pure 4-hydroxy-3-phenylbenzoic acid.

This may be achieved through acylation of the crude acid product under conventional conditions, using a reactive derivative of a carboxylic acid such as an acyl chloride or an anhydride. Functional derivatives of the lower aliphatic carboxylic acids (i.e., those containing up to 7 carbon atoms) are preferred, with derivatives of acetic acid and especially acetic anhydride being particularly preferred. The pure acylated product may then be isolated and reconverted to the free acid by conventional means if desired, or it may be used as such in the formation of polyesters by transesterification.

The invention is illustrated by the following examples. All percentages are by weight. The word "yield" wherever employed in the examples means the amount of 4-hydroxy-3-phenylbenzoic acid or salt thereof obtained, expressed as a percentage of total carboxylated material. The word "conversion" means the amount of reactant (2-phenylphenol) actually converted to carboxylated product, also expressed as a percentage. All percentages are by weight. Yields, conversions and impurities were determined by high pressure liquid chromatography unless actual isolation of the product is described.

EXAMPLE 1

A mixture of 526.36 grams (3.092 moles) of 2-phenylphenol, a 45% aqueous solution containing 171.79 grams (3.062 moles) of potassium hydroxide and 2000 ml. of toluene was heated to reflux under nitrogen, with stirring, and the water which passed over was collected in a Dean-Stark trap. When all water had been removed by azeotropic distillation, the mixture was cooled and anhydrous potassium 2-phenylphenate was isolated in nearly quantitative yield by filtration and dried under vacuum at 120° C.

A solution of 31.79 grams (150 mmol.) of the anhydrous potassium 2-phenylphenate in 72.7 grams of anhydrous dimethylformamide (30% solution) was heated to 100° C. under nitrogen and carbon dioxide was passed in at that temperature for 10 hours, with stirring. Analysis showed a conversion of 46.5%. The yield of potassium 4-hydroxy-3-phenylbenzoate was 95.2%.

EXAMPLE 2

A mixture of 255 grams (1.5 moles) of 2-phenylphenol, 102 grams (1.575 moles) of potassium hydroxide pellets (containing 87.1% potassium hydroxide with the balance being water) and 1000 ml. of toluene was heated under reflux in a nitrogen atmosphere, with removal of water as in Example 1. The toluene was removed by distillation and 755.6 grams of anhydrous dimethylformamide was added, to form a 29% solution.

The solution was cooled to 125° C. and carbon dioxide was passed in at that temperature for 8 hours, with stirring. After cooling to room temperature, the mixture was acidified with aqueous hydrochloric acid solution to a pH of 2 and extracted with toluene. The toluene solution was extracted with aqueous sodium carbonate to form the sodium salt, which was reacidified to yield a solid precipitate which was recrystallized from an isopropanol-water mixture. There was obtained 148.2 grams of a pale pink solid (46% conversion), for a yield of 94.7% 4-hydroxy-3-phenylbenzoic acid.

EXAMPLES 3-8

The procedure of Example 2 was repeated, using various 2-phenylphenol salts, amides, temperatures and reaction times. The results are given in Table I, with "DMF" meaning dimethylformamide and "DMAc" meaning dimethylacetamide.

TABLE I

| | Example | | | | | |
|---|---|---|---|---|---|---|
| | 3 | 4 | 5 | 6 | 7 | 8 |
| Salt cation | K | K | Na | Na | Na | K |
| Amide | DMF | DMF | DMF | DMF | DMF | DMAc |
| Temperature, °C. | 80 | 150 | 100 | 125 | 150 | 125 |
| Time, hours | 8 | 8 | 2 | 6 | 2 | 8 |
| Conversion, % | 43 | 43 | 27 | 22 | 44 | 50 |
| Yield, % | 96 | 95 | 91 | 93 | 86 | 89 |

EXAMPLES 9-11

The procedure of Example 2 was repeated, employing a reaction time of 5 hours and varying the proportion of 2-phenylphenol to provide salt solutions of various concentrations in the dimethylformamide. The results are given in Table II.

TABLE II

| | Example | | |
|---|---|---|---|
| | 9 | 10 | 11 |
| Salt, % | 14 | 30 | 40 |
| Conversion, % | 50 | 53 | 36 |
| Yield, % | 97 | 94 | 90 |

EXAMPLE 12

A mixture of 85 grams (500 mmol.) of 2-phenylphenol, 34 grams (525 mmol.) of 87.1% potassium hydroxide pellets and 500 ml. of toluene was heated under nitrogen for 4 hours, with stirring, as water was removed in accordance with Example 2. Approximately 250 ml. of the toluene was removed by distillation and 236 grams of dimethylformamide was added, after which the remaining toluene was removed by distillation to yield a 31% solution.

The mixture was cooled, transferred to an autoclave, pressurized to 17 atmospheres with carbon dioxide and heated for 4 hours at 75° C. It was again cooled and the contents were dissolved in water and acidified with aqueous hydrochloric acid solution. Upon extraction as described in Example 2, the desired product was obtained in 58% conversion; it comprised 94% of the desired 4-hydroxy-3-phenylbenzoic acid. Recrystallization from a mixture of water and isopropanol yielded 56.8 grams of purified product (conversion 49%, yield 97.8%).

EXAMPLES 13-17

The procedure of Example 12 was repeated, employing various salt concentrations, amides, carbon dioxide pressures, temperatures and reaction times. The results are listed in Table III. All yields are calculated from the crude product.

TABLE III

| | Example | | | | |
|---|---|---|---|---|---|
| | 13 | 14 | 15 | 16 | 17 |
| Amide | DMAc | DMF | DMAc | DMF | DMF |
| Salt, % | 30 | 30 | 30 | 42 | 30 |
| Pressure, ats. | 17.0 | 13.6 | 13.6 | 32.7 | 40.8 |
| Time, hrs. | 4 | 1 | 1 | 10 | 2 |
| Temperature, °C. | 75 | 100 | 100 | 100 | 100 |
| Conversion, % | 43 | 59 | 60 | 74 | 58 |
| Yield, % | 93 | 91 | 82 | 85 | 91 |

EXAMPLE 18

Following the procedure of Example 2, anhydrous potassium 2-phenylphenate was prepared from 3.223 moles of 2-phenylphenol in toluene. The toluene was removed and replaced by 944.5 grams of dimethylformamide. The solution was cooled to 100° C. and carbon dioxide was passed in for 6 hours, with stirring. At the end of this time, the conversion was 48.6%.

The solution was cooled to about 60° C. and 16.1 grams (537 mmol.) of an 80% (by weight) dispersion of sodium hydride in mineral oil was added. The mixture was stirred for 4 hours at 60° C., with two additional portions of sodium hydride being added during the last 2 hours.

The resulting thick purple mixture was stirred in a carbon dioxide atmosphere and heated to 100° C. over 4 hours. Heating at 100° C. was continued overnight, after which the conversion was 73.9%. In the next 2 hours, 806 mmol. of additional sodium hydride was added in two portions, after which heating with carbon dioxide at 100° C was continued for 8 hours. The conversion had then reached 79%.

About one third of the mixture was added to 2000 ml. of vigorously stirred toluene. The supernatent liquid was removed by decantation and the heavy viscous layer was extracted two more times with 500-ml. portions of toluene, dissolved in 500 ml. of water and acidified with aqueous hydrochloric acid solution. The product which precipitated was washed with water and dried to yield 562.6 grams of the desired 4-hydroxy-3-phenylbenzoic acid (82% conversion).

EXAMPLE 19

Crude 4-hydroxy-3-phenylbenzoic acid was prepared by the procedure of Example 5. To 190.2 grams thereof (889 mmol.) was added 300 ml. of glacial acetic acid. The mixture was heated to dissolve the crude product and filtered. There were then added 172.8 grams (1.69 moles) of acetic anhydride and 1 gram of pyridine, and the mixture was heated under reflux for 15 hours and cooled. A white crystalline precipitate formed and was collected by filtration, washed with cold acetic acid and dried to yield 182.2 grams (86.8% conversion) of 4-acetoxy-3-phenylbenzoic acid, melting at 187° C. It was shown by analysis to be 99.6% pure.

What is claimed is:

1. A method for preparing 4-hydroxy-3-phenylbenzoic acid which comprises contacting a mixture of an anhydrous alkali metal salt of 2-phenylphenol and a liquid N,N-dialkylcarboxamide, said mixture containing up to about 50% by weight of said salt, with carbon dioxide at a pressure of at least about one atmosphere and a temperature in the range of about 70°–150° C., and neutralizing the salt thus formed.

2. A method according to claim 1 wherein the carboxamide is dimethylformamide or dimethylacetamide.

3. A method according to claim 2 wherein the salt is a sodium or potassium salt.

4. A method according to claim 3 wherein the temperature is in the range of about 80°–110° C.

5. A method according to claim 4 wherein the carbon dioxide is passed into the mixture at atmospheric pressure.

6. A method according to claim 4 wherein the carboxamide is dimethylformamide.

7. A method according to claim 6 wherein the salt is a potassium salt.

8. A method according to claim 5 wherein an anhydrous base is added to the reaction mixture when the carbonation reaction has ceased.

9. A method according to claim 8 wherein the base is sodium amide or sodium hydride.

10. A method according to claim 9 wherein the base is sodium hydride.

11. A method according to claim 4 wherein the carbon dioxide is pressurized with the mixture at a pressure in the range of about 1–50 atmospheres.

12. A method according to claim 11 wherein the carboxamide is dimethylformamide.

13. A method according to claim 12 wherein the salt is a potassium salt.

14. A method according to claim 4 wherein the crude product is purified by extraction with a non-polar solvent effective to dissolve non-polar and weakly polar materials.

15. A method according to claim 14 wherein the solvent is toluene.

16. A method according to claim 4 wherein the crude acid product is acylated with an acyl chloride or an anhydride and the acylated product is isolated.

17. A method according to claim 16 wherein the acylating reagent is acetic anhydride.

* * * * *